United States Patent
Kiyose et al.

(10) Patent No.: US 10,042,044 B2
(45) Date of Patent: Aug. 7, 2018

(54) ULTRASONIC DEVICE, PROBE, ELECTRONIC DEVICE, AND ULTRASONIC IMAGING APPARATUS

(71) Applicant: SEIKO EPSON CORPORATION, Tokyo (JP)

(72) Inventors: Kanechika Kiyose, Nagano (JP); Hiroshi Matsuda, Gifu (JP); Daisuke Nakanishi, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 876 days.

(21) Appl. No.: 14/495,145

(22) Filed: Sep. 24, 2014

(65) Prior Publication Data
US 2015/0092514 A1   Apr. 2, 2015

(30) Foreign Application Priority Data
Sep. 30, 2013  (JP) ................. 2013-203478

(51) Int. Cl.
*B06B 1/06* (2006.01)
*G01S 7/52* (2006.01)
(Continued)

(52) U.S. Cl.
CPC ........ *G01S 7/52017* (2013.01); *A61B 8/4494* (2013.01); *B06B 1/0629* (2013.01); *G01S 15/8925* (2013.01); *H01L 41/0825* (2013.01)

(58) Field of Classification Search
USPC ........................................ 367/140
See application file for complete search history.

(56) References Cited

U.S. PATENT DOCUMENTS 4,433,400 A * 2/1984 DeReggi ............... B06B 1/0688
                                                310/800
5,456,259 A * 10/1995 Barlow .................... A61B 8/12
                                                600/459
(Continued)

FOREIGN PATENT DOCUMENTS

| JP | 2007-229328 A | 9/2007 | |
| JP | 2012-109800 A | 6/2012 | |
| KR | 20120066503 A | * 6/2012 | ........... B06B 1/0292 |

OTHER PUBLICATIONS

Bavaro, Vito, Giosue Caliano, and Massimo Pappalardo. "Element shape design of 2-D CMUT arrays for reducing grating lobes." IEEE transactions on ultrasonics, ferroelectrics, and frequency control 55.2 (2008): 308-318.*

*Primary Examiner* — Isam A Alsomiri
*Assistant Examiner* — Jonathan D Armstrong (57) ABSTRACT

An ultrasonic device includes a base in which a base layer of a vibrating film is formed in every opening that is disposed in an array; an interconnect layer, which is a conductor, formed on the base layer; an insulating film that is formed on the interconnect layer, and forms a laminated structure with respect to the base layer; a plurality of piezoelectric elements that are separated from the interconnect layer by the insulating film, the piezoelectric elements each including a first electrode and a second electrode that sandwich a piezoelectric film on the insulating film; and a through conductor that passes through the insulating film, and connects at least one of the first electrode and the second electrode to the conductor constituting the interconnect layer.

7 Claims, 8 Drawing Sheets

(51) Int. Cl.
  *H01L 41/08* (2006.01)
  *G01S 15/89* (2006.01)
  *A61B 8/00* (2006.01)

(56) References Cited

U.S. PATENT DOCUMENTS

| | | | | |
|---|---|---|---|---|
| 5,465,724 A * | 11/1995 | Sliwa, Jr. | | A61B 8/12 600/459 |
| 5,467,779 A * | 11/1995 | Smith | | A61B 8/12 600/445 |
| 5,522,878 A * | 6/1996 | Montecalvo | | A61B 8/4281 600/437 |
| 5,617,866 A * | 4/1997 | Marian, Jr. | | A61B 8/00 439/66 |
| 5,625,149 A * | 4/1997 | Gururaja | | B06B 1/064 310/334 |
| 5,732,706 A * | 3/1998 | White | | A61B 8/4483 600/437 |
| 5,792,058 A * | 8/1998 | Lee | | B06B 1/0622 600/459 |
| 5,795,299 A * | 8/1998 | Eaton | | A61B 8/12 600/459 |
| 5,857,974 A * | 1/1999 | Eberle | | A61B 1/0011 29/25.35 |
| 5,967,986 A * | 10/1999 | Cimochowski | | A61B 5/0031 600/454 |
| 6,039,689 A * | 3/2000 | Lizzi | | A61N 7/02 600/439 |
| 6,093,150 A * | 7/2000 | Chandler | | A61B 8/12 600/459 |
| 6,159,149 A * | 12/2000 | Erikson | | A61B 8/4483 600/437 |
| 6,210,339 B1 * | 4/2001 | Kiepen | | A61B 5/0215 600/372 |
| 6,271,620 B1 * | 8/2001 | Ladabaum | | B06B 1/0292 310/334 |
| 6,457,365 B1 * | 10/2002 | Stephens | | A61B 8/12 600/447 |
| 6,776,758 B2 * | 8/2004 | Peszynski | | A61B 8/12 600/437 |
| 6,936,008 B2 * | 8/2005 | Tarakci | | A61B 8/08 600/437 |
| 7,087,023 B2 * | 8/2006 | Daft | | B06B 1/0292 600/459 |
| 7,226,417 B1 * | 6/2007 | Eberle | | B06B 1/0633 29/25.35 |
| 7,314,447 B2 * | 1/2008 | Park | | A61B 8/00 600/459 |
| 7,441,321 B2 * | 10/2008 | Baumgartner | | B06B 1/0292 216/62 |
| 7,489,593 B2 * | 2/2009 | Nguyen-Dinh | | B06B 1/0292 367/181 |
| 7,500,954 B2 * | 3/2009 | Wilser | | A61B 8/12 600/459 |
| 7,514,851 B2 * | 4/2009 | Wilser | | B06B 1/0292 310/334 |
| 7,612,483 B2 * | 11/2009 | Degertekin | | B06B 1/0292 310/309 |
| 7,773,033 B2 * | 8/2010 | Morton | | H01P 1/2005 333/24.2 |
| 7,775,979 B2 * | 8/2010 | Thomenius | | G01S 7/5208 600/437 |
| 7,785,098 B1 * | 8/2010 | Appleby | | B29C 33/302 264/319 |
| 7,898,464 B1 * | 3/2011 | Anderson | | H01Q 3/2676 342/175 |
| 7,973,696 B2 * | 7/2011 | Puscasu | | G01J 3/108 342/1 |
| 8,120,229 B2 * | 2/2012 | Huang | | B06B 1/0292 310/309 |
| 8,483,014 B2 * | 7/2013 | Huang | | B06B 1/0292 367/181 |
| 8,508,106 B2 * | 8/2013 | Bauer | | A61B 17/225 310/334 |
| 8,636,649 B1 * | 1/2014 | Gazdzinski | | A61B 1/00016 600/109 |
| 8,643,532 B1 * | 2/2014 | Puscasu | | H01Q 15/0066 342/1 |
| 8,852,112 B2 * | 10/2014 | Bielewicz | | A61B 8/12 600/437 |
| 8,858,447 B2 * | 10/2014 | Chung | | B32B 37/14 310/309 |
| 8,864,675 B2 * | 10/2014 | Dietz | | A61B 8/12 600/437 |
| 8,880,141 B2 * | 11/2014 | Chen | | A61B 5/0091 367/181 |
| 9,096,418 B2 * | 8/2015 | Hong | | B81B 3/0027 |
| 9,096,422 B2 * | 8/2015 | Hajati | | B81B 7/008 |
| 9,312,470 B2 * | 4/2016 | Rice | | B06B 1/0662 |
| 9,320,465 B2 * | 4/2016 | Kline | | A61B 5/036 |
| 9,345,449 B2 * | 5/2016 | Stein | | A61B 5/4528 |
| 9,402,598 B2 * | 8/2016 | Yoshimura | | A61B 8/4444 |
| 9,404,959 B2 * | 8/2016 | Takahashi | | B06B 1/0622 |
| 9,408,588 B2 * | 8/2016 | Huang | | A61B 8/12 |
| 9,505,030 B2 * | 11/2016 | Rothberg | | A61B 8/4494 |
| 9,520,811 B2 * | 12/2016 | Johnson | | B06B 1/0292 |
| 9,603,580 B2 * | 3/2017 | Chaggares | | B06B 1/0622 |
| 9,629,586 B2 * | 4/2017 | Ghaffari | | A61B 5/6879 |
| 9,647,187 B1 * | 5/2017 | Yap | | H01L 33/64 |
| 9,647,195 B2 * | 5/2017 | Hajati | | H01L 41/0475 |
| 9,662,069 B2 * | 5/2017 | De Graff | | A61B 18/1492 |
| 9,684,074 B2 * | 6/2017 | Schrank | | G01S 17/026 |
| 9,726,755 B2 * | 8/2017 | Kitchens, II | | G01S 7/539 |
| 9,737,735 B2 * | 8/2017 | Dietz | | A61N 7/00 |
| 9,789,515 B2 * | 10/2017 | Hajati | | B06B 1/0622 |
| 9,818,926 B2 * | 11/2017 | Suzuki | | G01N 29/2437 |
| 9,861,268 B2 * | 1/2018 | Gazdzinski | | A61B 1/041 |
| 9,861,296 B2 * | 1/2018 | Gazdzinski | | A61B 5/073 |
| 9,868,137 B2 * | 1/2018 | Kiyose | | B06B 1/0622 |
| 9,899,371 B2 * | 2/2018 | Rothberg | | H01L 27/0617 |
| 9,907,538 B2 * | 3/2018 | Chaggares | | A61B 8/4494 |
| 9,910,017 B2 * | 3/2018 | Rothberg | | G01N 29/2406 |
| 9,910,018 B2 * | 3/2018 | Rothberg | | G01N 29/2406 |
| 9,913,575 B2 * | 3/2018 | Gazdzinski | | A61B 8/12 |
| 9,915,726 B2 * | 3/2018 | Bailey | | G01S 7/481 |
| 9,915,733 B2 * | 3/2018 | Fried | | G01S 17/89 |
| 9,952,323 B2 * | 4/2018 | Deane | | G01S 17/89 |
| 9,974,518 B2 * | 5/2018 | Rice | | A61B 8/4483 |
| 2003/0009873 A1 * | 1/2003 | Hatangadi | | B06B 1/0607 29/594 |
| 2004/0100163 A1 * | 5/2004 | Baumgartner | | B06B 1/0622 310/334 |
| 2005/0200242 A1 * | 9/2005 | Degertekin | | B06B 1/0292 310/334 |
| 2005/0218488 A1 * | 10/2005 | Matsuo | | B81C 1/00095 257/678 |
| 2006/0116585 A1 * | 6/2006 | Nguyen-Dinh | | B06B 1/0292 600/459 |
| 2009/0024039 A1 * | 1/2009 | Wang | | A61B 10/0233 600/459 |
| 2009/0076392 A1 * | 3/2009 | Oshiki | | G01S 15/8925 600/459 |
| 2009/0301199 A1 * | 12/2009 | Azuma | | A61B 8/08 73/603 |
| 2010/0201222 A1 * | 8/2010 | Adachi | | A61B 8/4483 310/317 |
| 2013/0286661 A1 * | 10/2013 | Holman | | G02B 26/0875 362/332 |

* cited by examiner

ULTRASONIC DEVICE, PROBE, ELECTRONIC DEVICE, AND ULTRASONIC IMAGING APPARATUS

BACKGROUND

1. Technical Field

The present invention relates to an ultrasonic device, and to a probe, an electronic device, an ultrasonic imaging apparatus, and the like using the same.

2. Related Art

Ultrasonic devices are generally known. An ultrasonic device includes ultrasonic transducer elements that are arranged in an array. A piezoelectric element is mounted on a vibrating film in each ultrasonic transducer element. The piezoelectric element is configured by a piezoelectric film sandwiched between an upper electrode and a lower electrode. A drive voltage is applied to the piezoelectric film from the upper electrode and the lower electrode when ultrasonic vibration is generated. The vibrating film ultrasonically vibrates. An ultrasonic image can be formed based on ultrasonic waves reflected from a subject.

The Resolution of an ultrasonic image can be increased by increasing the layout density of the ultrasonic transducer elements. In JP A-2012-109800, an interconnect width is reduced when the layout density is increased, since interconnects are laid out in the region between adjacent ultrasonic transducer elements. Reduction of the interconnect width causes an increase in an interconnect resistance. The increase in the interconnect resistance causes variation in operation timing between the ultrasonic transducer elements.

SUMMARY

According to at least one aspect of the invention, an ultrasonic device can be provided in which an increase of an interconnect resistance can be suppressed while increasing the layout density of ultrasonic transducer elements.

(1) An aspect of the invention relates to an ultrasonic device including a base in which a base layer of a vibrating film is formed every opening that is disposed in an array; an interconnect layer, which is a conductor, formed on the base layer; an insulating film that is formed on the interconnect layer, and forms a laminated structure on the base layer; a plurality of piezoelectric elements that are separated from the interconnect layer by the insulating film, the piezoelectric elements each including a first electrode and a second electrode that sandwich a piezoelectric film on the insulating film; and a through conductor that passes through the insulating film, and connects at least one of the first electrode and the second electrode to the conductor.

In the ultrasonic device, a laminated structure is established by the base layer and the insulating film. The base layer and the insulating film form a vibrating film. The piezoelectric element is formed on the vibrating film in the every opening. The vibrating film and the piezoelectric element form an ultrasonic transducer element. Here, the conductor constituting the interconnect layer is disposed under the insulating film. The conductor constituting the interconnect layer extends in a layer that is different from the first electrode and the second electrode of the piezoelectric element. Accordingly, the conductor can have a spread not interrupted by the first electrode and the second electrode. The conductor can function as a bus interconnect for the piezoelectric elements. Interconnect resistance can be reduced.

(2) The conductor constituting the interconnect layer has a width that is larger than a width of an interconnect that connects the first electrode and the second electrode of the piezoelectric elements that are adjacent to each other. The conductor constituting the interconnect layer can thereby function as a bus interconnect for the piezoelectric elements. Interconnect resistance can be reduced. The layout density of the piezoelectric elements and the layout density of the ultrasonic transducer elements can be increased, compared with the case in which a bus interconnect is laid out between the piezoelectric elements.

(3) The conductor constituting the interconnect layer may have a width that is larger than a width of an interconnect that connects the first electrodes or the second electrodes of the piezoelectric elements that are adjacent to each other. The conductor constituting the interconnect layer can thereby function as a bus interconnect for the piezoelectric elements. Interconnect resistance can be reduced. The layout density of the piezoelectric elements and the layout density of the ultrasonic transducer elements can be increased, compared with the case in which a bus interconnect is laid out between the piezoelectric elements.

(4) The interconnect layer can be formed by an unpatterned film of a conductive material that is connected to all the piezoelectric elements in the array in common. The unpatterned film can function as a common bus interconnect common to all the piezoelectric elements.

(5) The piezoelectric element can be arranged at an equal pitch in the array. In the array, a drive voltage is supplied to the piezoelectric elements, segment by segment, in a sequence according to line scanning or sector scanning. The vibrating film vibrates according to the supply of the drive voltage. Since the piezoelectric elements are arranged at an equal pitch, contamination by unwanted noise in transmitting ultrasonic waves can be avoided.

(6) The interconnect layer can be formed by an unpatterned film of a conductive material that is connected to the piezoelectric elements in common for each segment of the array. A signal can be supplied from the unpatterned film in each segment. The interconnect layer can thereby function as a signal line.

(7) The piezoelectric element can be arranged at an equal pitch at least in the segment. A drive voltage is supplied to the piezoelectric elements in the segment when ultrasonic waves are transmitted. The vibrating film vibrates simultaneously according to the supply of the drive voltage. Since the piezoelectric elements are arranged at an equal pitch, contamination by unwanted noises in transmitting ultrasonic waves can be avoided.

(8) The ultrasonic device can be used by being incorporated in a probe. Here, the probe may include the ultrasonic device and a casing that supports the ultrasonic device.

(9) The ultrasonic device can be used by being incorporated in an electronic device. Here, the electronic device may include the ultrasonic device and a processing apparatus that is connected to the ultrasonic device and processes an output of the ultrasonic device.

(10) The ultrasonic device can be used by being incorporated in an ultrasonic imaging apparatus. Here, the ultrasonic imaging apparatus can include the ultrasonic device, and a display apparatus that displays an image that is generated from an output of the ultrasonic device.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, an embodiment of the invention will be described with reference to the attached drawings. Note that the embodiment described below is not intended to unduly limit the content of the invention recited in the claims, and all of the constituent elements described in the embodiment are not necessarily essential as solutions provided by the invention.

(1) Overall Configuration of Ultrasonic Diagnostic Apparatus

Figure 1:
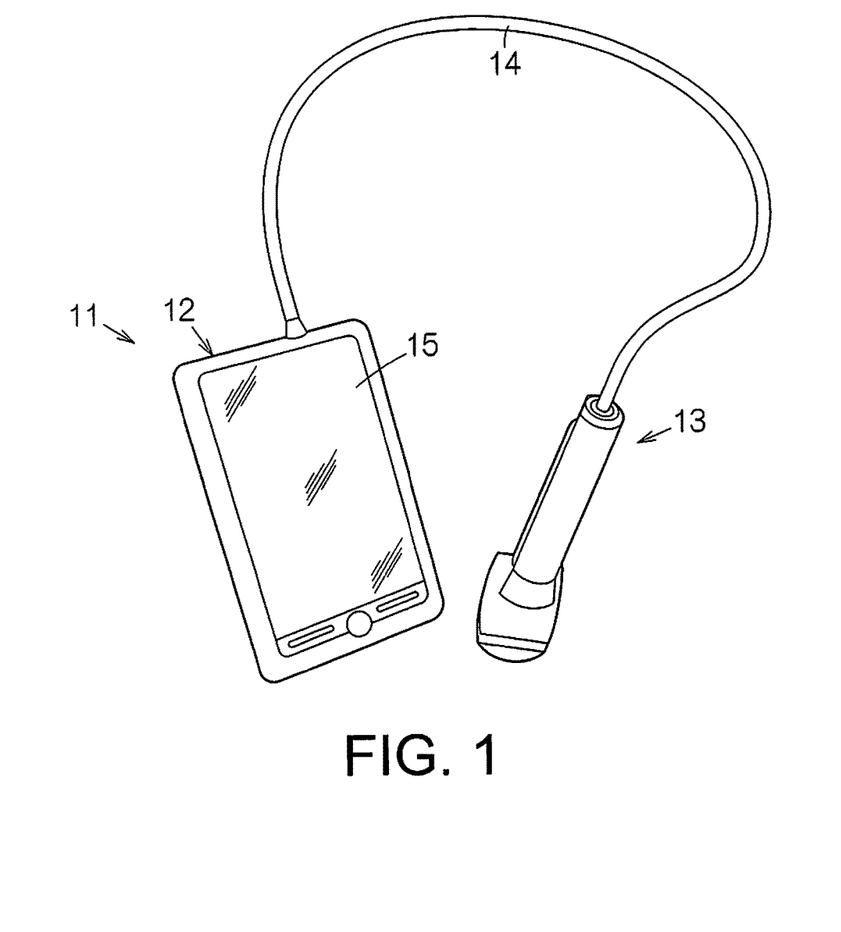
FIG. 1 is an external view schematically showing a specific example of an electronic device, that is, an ultrasonic diagnostic apparatus.

FIG. 1 schematically shows a configuration of a specific example of an electronic device, that is, an ultrasonic diagnostic apparatus (ultrasonic imaging apparatus) 11. The ultrasonic diagnostic apparatus 11 includes an apparatus terminal (processing apparatus) 12 and an ultrasonic probe (probe) 13. The apparatus terminal 12 and the ultrasonic probe 13 are connected to each other with a cable 14. The apparatus terminal 12 and the ultrasonic probe 13 send and receive electric signals through the cable 14. A display panel (display apparatus) 15 is incorporated in the apparatus terminal 12. A screen of the display panel 15 is exposed at the surface of the apparatus terminal 12. An image is generated in the apparatus terminal 12 based on the ultrasonic waves detected by the ultrasonic probe 13. An imaged detection result is displayed on the screen of the display panel 15.

Figure 2:
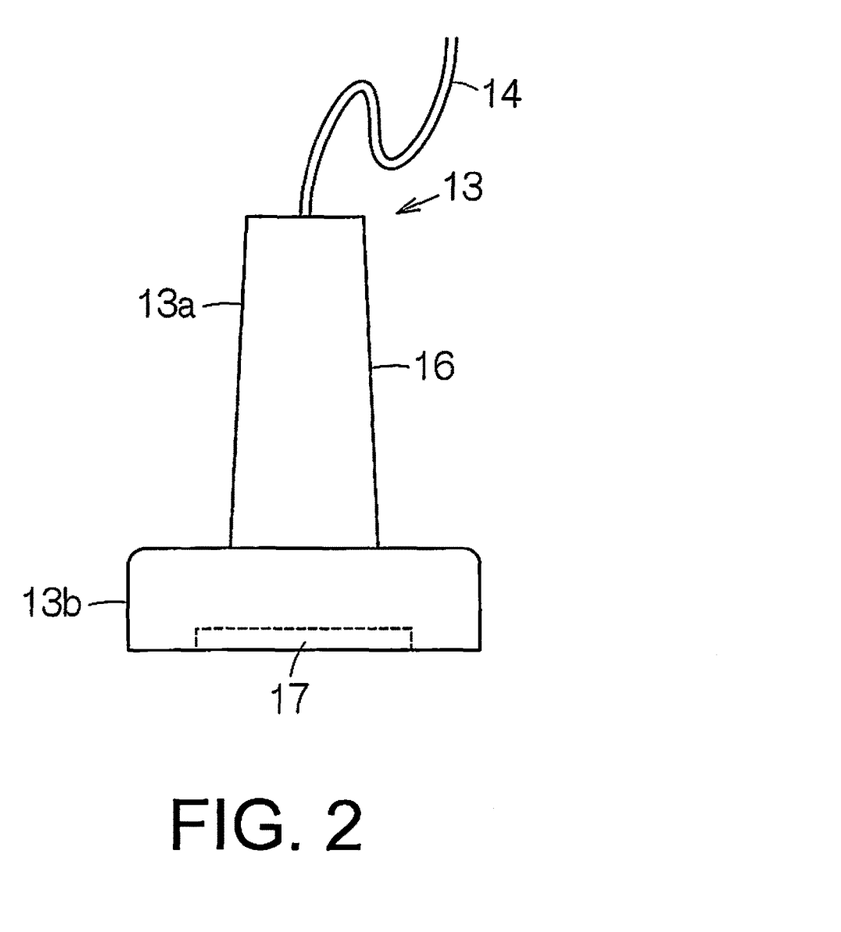
FIG. 2 is an enlarged front view of an ultrasonic probe.

The ultrasonic probe 13 has a casing 16, as shown in FIG. 2. The ultrasonic device 17 is housed in the casing 16. The surface of the ultrasonic device 17 can be exposed at the surface of the casing 16. The ultrasonic device 17 outputs ultrasonic waves from the surface thereof and receives reflected waves of the ultrasonic waves. In addition, the ultrasonic probe 13 may include a probe head 13b that is detachably coupled to a probe main body 13a. Here, the ultrasonic device 17 can be incorporated in the casing 16 of the probe head 13b.

Figure 3:
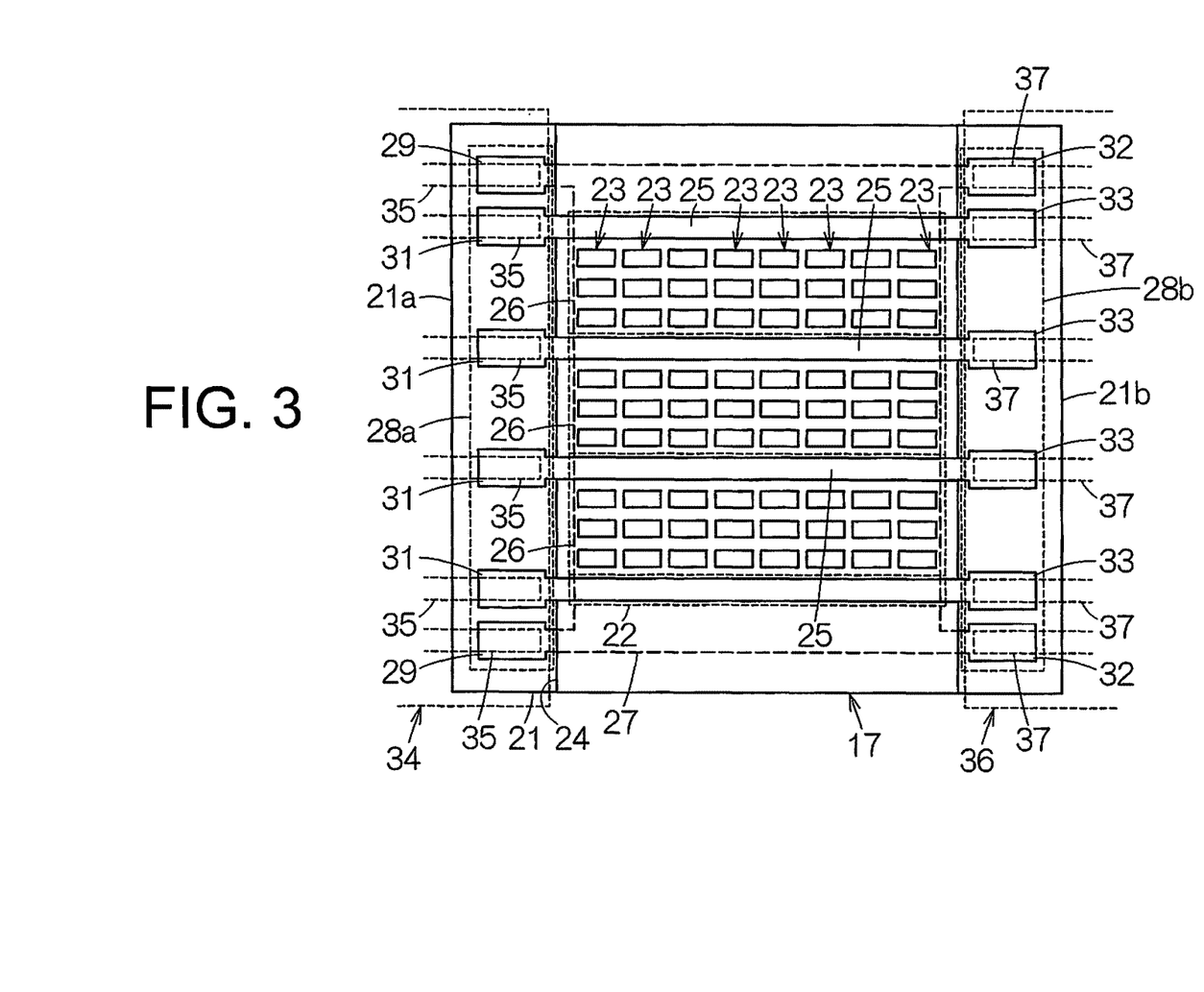
FIG. 3 is an enlarged plan view of an ultrasonic device according to a first embodiment.

FIG. 3 shows a plan view of an ultrasonic device 17 according to a first embodiment. The ultrasonic device 17 includes a base 21. An element array 22 is formed on the base 21. The element array 22 is configured by an arrangement of ultrasonic transducer elements (hereinafter referred to as "elements") 23. The array is formed by a matrix of a plurality of rows and columns. In addition, a staggered layout may be established in the array. In the staggered layout, a group of elements 23 in even columns may be shifted by half a row pitch relative to a group of elements 23 in odd columns. The number of elements in each odd column may be smaller by one or larger by one relative to the number of elements in each even column. The ultrasonic device 17 is configured as one ultrasonic transducer element chip.

An insulating film 24 is overlaid on the surface of the base 21. The insulating film 24 is formed by zirconium oxide ($ZrO_2$), for example. The insulating film 24 is spread over the whole surface of the base 21. A plurality of bus interconnects 25 are laid out on the surface of the insulating film 24. The bus interconnects 25 extend along the column direction of the array in parallel to each other. Here, one bus interconnect 25 is assigned for every three columns of elements 23. The bus interconnects 25 divide the element array 22 into a plurality of segments 26. Titanium (Ti), iridium (Ir), and a stacked film constituted by platinum (Pt) and titanium (Ti), for example, can be used for the bus interconnects 25. Note that the other conductive materials may be used for the bus interconnects 25.

An interconnect layer 27, which is a conductor, is formed, under the insulating film 24, on the surface of the base 21. The interconnect layer 27 is formed by an unpatterned film of a conductive material. Iridium (Ir), for example, can be used for the conductive material. Note that the other conductive materials may be used for the interconnect layer 27. The interconnect layer 27 is separated from the bus interconnects 25 by the insulating film 24. The interconnect layer 27 functions as one common bus interconnect for all the elements 23.

Energization of elements 23 is switched every segment 26. Linear scanning and sector scanning can be realized according to such energization switching. Since the elements 23 in one segment 26 output ultrasonic waves simultaneously, the number of elements in one segment 26, that is the number of rows in the array, can be determined in accordance with the output level of the ultrasonic waves. The number of rows may be set to 10 to 15 rows, for example. In the drawing, the rows are partially omitted, and eight rows are drawn. The number of columns of the array can be determined in accordance with the extent of the range of the scan. The number of columns may be set to 128 columns or 256 columns, for example. In the drawing, the columns are partially omitted, and nine columns are depicted.

The outline of the base 21 has a first edge 21a and a second edge 21b that oppose each other in parallel. One line of a first terminal array 28a is laid out between the first edge 21a and an outline of the element array 22. One line of a second terminal array 28b is laid out between the second edge 21b and the outline of the element array 22. The first terminal array 28a can form one line parallel to the first edge 21a. The second terminal array 28b can form one line parallel to the second edge 21b. The first terminal array 28a is configured by a pair of common interconnect terminals 29 and a plurality of signal interconnect terminals 31. Similarly, the second terminal array 28b is configured by a pair of common interconnect terminals 32 and a plurality of signal interconnect terminals 33. The common interconnect terminals 29 and 32 are connected to the interconnect layer 27. Two ends of one bus interconnect 25 are connected to the signal interconnect terminals 31 and 33, respectively. Here, the outline of the base 21 has a rectangular shape. Alternatively, the outline of the base 21 may have a square shape or a trapezoidal shape.

A first flexible printed wiring board (hereinafter referred to as "first wiring board") 34 is coupled to the base 21. The first wiring board 34 is overlaid on the first terminal array 28a. Conductive lines, that is, first signal lines 35 are formed on one end of the first wiring board 34 in one-to-one correspondence with the common interconnect terminals 29 and the signal interconnect terminals 31. The first signal lines 35 respectively face and are joined to the common interconnect terminals 29 and signal interconnect terminals 31. Similarly, a second flexible printed wiring board (hereinafter referred to as "second wiring board") 36 is coupled to the base 21. The second wiring board 36 is overlaid on the second terminal array 28b. Conductive lines, that is, second signal lines 37 are formed on one end of the second wiring board 36 in one-to-one correspondence with the common interconnect terminals 32 and the signal interconnect terminals 33. The second signal lines 37 respectively face and are joined to the common interconnect terminals 32 and signal interconnect terminals 33.

Figure 4:
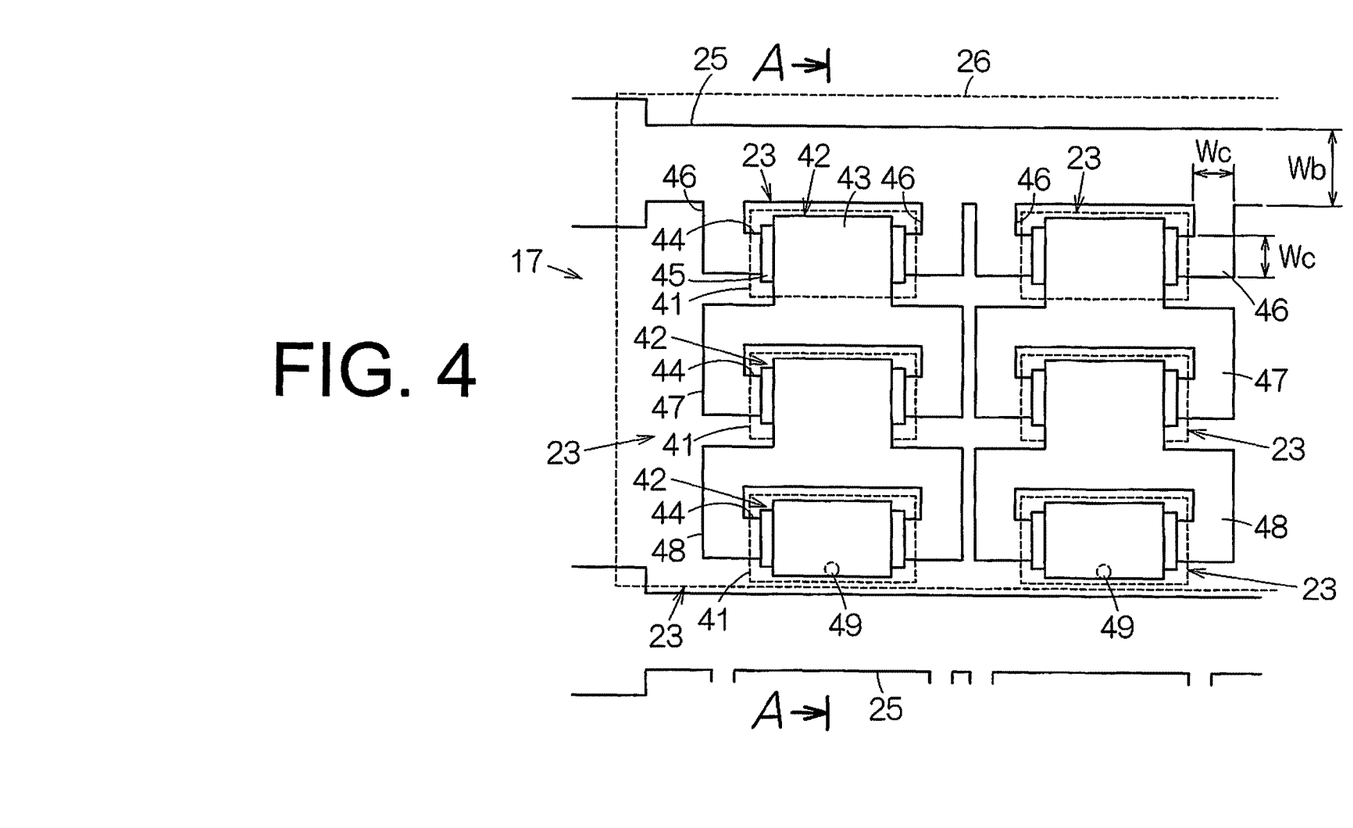
FIG. 4 is an enlarged partial plan view of the ultrasonic device.

FIG. 4 shows an enlarged partial plan view of the ultrasonic device 17. Each element 23 includes a vibrating film 41. The detail of the vibrating film 41 will be described later. In FIG. 4, an outline of the vibrating film 41 is depicted by a dashed line in plan view from a direction perpendicular to the film face of the vibrating film 41 (plan view in a thickness direction of the substrate). The inside of the outline corresponds to the inside of the region of the vibrating film 41. The outside of the outline corresponds to the outside of the region of the vibrating film 41. A piezoelectric element 42 is formed on the vibrating film 41. In the piezoelectric element 42, a piezoelectric film 45 is sandwiched between an upper electrode (first electrode) 43 and a lower electrode (second electrode) 44, as described later. The lower electrode 44, the piezoelectric film 45, and the upper electrode 43 are stacked in order. The upper electrode 43 and the lower electrode 44 may be formed by the similar conductive material to that of the bus interconnect 25. The upper electrode 43 and the lower electrode 44 extend in directions orthogonal to each other. Here, the upper electrode 43 extends in the row direction of the array, and the lower electrode 44 extends in the column direction of the array, for example. The piezoelectric film 45 may be formed by lead zirconate titanate (PZT), for example. Other piezoelectric materials may be used for the piezoelectric film 45.

A first interconnect 46, a second interconnect 47, and a third interconnect 48 are formed on the surface of the insulating film 24 in each segment 26. The first interconnect 46 connects an element 23 in a first column to the corresponding bus interconnect 25. The first interconnect 46 is continuous from the corresponding bus interconnect 25 to a lower electrode 44 of the element 23. The second interconnect 47 connects a lower electrode 44 of an element 23 in a second column to an upper electrode 43 of the element 23 in the first column. The second interconnect 47 is continuous from the upper electrode 43 of the element 23 in the first column to the lower electrode 44 of the element 23 in the second column. The third interconnect 48 connects a lower electrode 44 of an element 23 in a third column to an upper electrode 43 of the element 23 in the second column. The third interconnect 48 is continuous from the upper electrode 43 of the element 23 in the second column to the lower electrode 44 of the element 23 in the third column. The first interconnect 46, the second interconnect 47, and the third interconnect 48 can be formed by a similar conductive material as that of the bus interconnect 25, for example. Here, the first interconnect 46, the second interconnect 47, and the third interconnect 48 have the same width Wc. The width Wb of the bus interconnect 25 is larger than the width Wc of the first interconnect 46, the second interconnect 47, and the third interconnect 48. Moreover, the width of the interconnect layer 27 is larger than the width Wc of the first interconnect 46, the second interconnect 47, and the third interconnect 48, since the interconnect layer 27 is spread over the entire surface of the base 21.

A through conductor 49 is embedded in the insulating film 24 in each element 23 in the third column. The through conductor 49 passes through the insulating film 24 from the surface of the insulating film 24 to the surface of the interconnect layer 27, as is clear from FIG. 5. The through conductor 49 connects an upper electrode 43 of the element 23 in the third column to the interconnect layer 27. The through conductor 49 may be continuous from the upper electrode 43 of the element 23 in the third column to the interconnect layer 27. The through conductor 49 can be formed by a similar conductive material as that of the upper electrode 43. The elements 23 in the same row are thereby electrically connected in series between the bus interconnect 25 and the interconnect layer 27.

Figure 5:
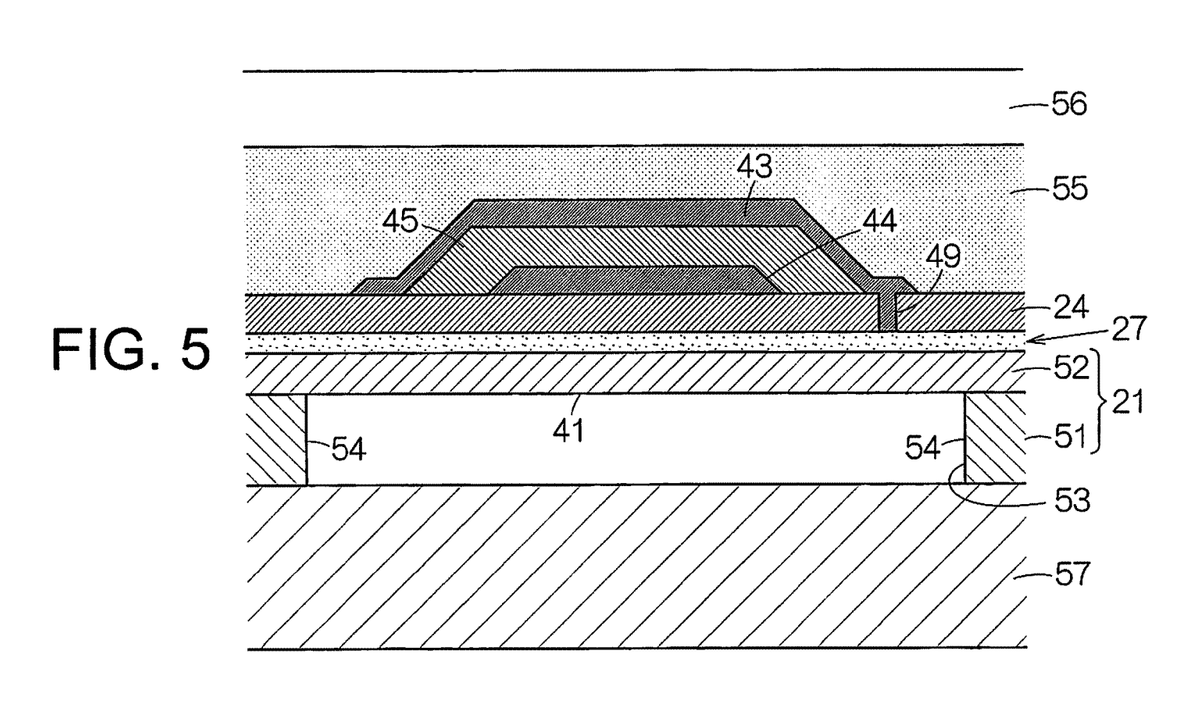
FIG. 5 is an enlarged cross-sectional view taken along line A-A in FIG. 4.

The base 21 includes a plate material 51 and a surface layer film 52, as shown in FIG. 5. The surface layer film 52 is formed on the whole surface of the plate material 51. The plate material 51 is formed by silicon (Si), for example. The surface layer film 52 is formed by a silicon oxide ($SiO_2$) layer, for example. The silicon oxide layer is spread over the whole surface of the silicon substrate. The silicon oxide layer can be integrally formed on the silicon substrate due to thermal oxidation processing performed on the silicon substrate.

An opening 53 is formed in the plate material 51 in each element 23. The openings 53 are disposed in an array in the plate material 51. An outline of the region in which the openings 53 are disposed corresponds to the outline of the element array 22. A partition wall 54 is defined between two adjacent openings 53. Adjacent openings 53 are partitioned by the partition wall 54. The wall thickness of the partition wall 54 corresponds to a space between the openings 53. The partition wall 54 defines two wall faces in planes that are spread in parallel to each other. The wall thickness corresponds to the distance between the two wall faces. That is, the wall thickness can be defined by a length of a perpendicular line that is sandwiched by the wall faces and is perpendicular to the wall faces.

The interconnect layer 27 is overlaid on the surface of the surface layer film 52. The interconnect layer 27 adheres closely to the surface of the surface layer film 52. The insulating film 24 is overlaid on the surface of the interconnect layer 27. The insulating film 24 thereby forms a laminated structure with respect to the surface layer film 52. The surface layer film 52, the interconnect layer 27, and the insulating film 24 form a flexible film. The surface layer film 52 is adjacent to the opening 53. A part of the flexible film corresponding to the outline of the opening 53 forms the vibrating film 41. The surface layer film 52 thereby forms a base layer of the vibrating film 41. The vibrating film 41 is a portion of the flexible film that can generate film vibration in a thickness direction of the plate material 51 since it faces the opening 53. The film thickness of the surface layer film 52 can be determined based on the resonance frequency.

The lower electrode 44, the piezoelectric film 45, and the upper electrode 43 are stacked in order on the surface of the vibrating film 41. The piezoelectric film 45 covers at least a portion of the lower electrode 44 and a portion of the vibrating film 41. The upper electrode 43 covers at least a portion of the piezoelectric film 45. Here, the piezoelectric film 45 completely covers the surface of the lower electrode 44, under the upper electrode 43. Due to the action of the piezoelectric film 45, a short circuit can be prevented between the upper electrode 43 and the lower electrode 44.

An acoustic matching layer 55 is stacked on the surface of the base 21. The acoustic matching layer 55 is overlaid on the whole surface of the base 21, for example. As a result, the acoustic matching layer 55 covers the element array 22, the first and second terminal arrays 28a and 28b, and the first and second wiring boards 34 and 36. The acoustic matching layer 55 adheres tightly to the surface of the elements 23. A silicone resin film, for example, can be used for the acoustic matching layer 55. The acoustic matching layer 55 protects the structure of the element array 22, joints between the first terminal array 28a and the first wiring board 34, and joints between the second terminal array 28b and the second wiring board 36.

An acoustic lens 56 is stacked on the acoustic matching layer 55. The acoustic lens 56 adheres tightly to a surface of the acoustic matching layer 55. An outer surface of the acoustic lens 56 is formed by a partial cylindrical face. The partial cylindrical face has a generatrix that is parallel to the row direction of the array. The curvature of the partial cylindrical face is determined according to the focal position of ultrasonic waves to be transmitted from one column of elements 23 that are connected to one line of the bus interconnect 25. The acoustic lens 56 is formed by a silicone resin, for example.

A reinforcing plate 57 is fixed to a rear face of the base 21. The rear face of the base 21 is placed on a surface of the reinforcing plate 57. The reinforcing plate 57 closes the opening 53 from the rear face of the ultrasonic device 17. The reinforcing plate 57 may include a rigid base material. The reinforcing plate 57 can be formed by a silicon substrate, for example. The plate thickness of the base 21 is set to around 100 μm, for example, and the plate thickness of the reinforcing plate 57 is set to around 100 to 150 μm, for example. Here, the partition wall 54 is coupled to the reinforcing plate 57. The reinforcing plate 57 is joined to each of the partition walls 54 via at least one joint region. An adhesive can be used for joining.

(2) Operation of Ultrasonic Diagnostic Apparatus

Next, operations of the ultrasonic diagnostic apparatus 11 will be described briefly. Pulse signals are supplied to the piezoelectric element 42 for transmitting ultrasonic waves. The pulse signals are supplied to the elements 23, every segment 26, through the common interconnect terminals 29 and 32 and the signal interconnect terminals 31 and 33. In each element 23, an electric field acts on the piezoelectric film 45 between the lower electrode 44 and the upper electrode 43. The piezoelectric film 45 vibrates ultrasonically. The vibration of the piezoelectric film 45 propagates to the vibrating film 41. The vibrating film 41 thereby vibrates ultrasonically. As a result, a desired ultrasonic beam is emitted toward an object (interior of a human body, for example).

Reflected waves of the ultrasonic waves vibrate the vibrating film 41. The ultrasonic vibration of the vibrating film 41 vibrates the piezoelectric film 45 at a desired frequency. A voltage is output from the piezoelectric element 42 due to piezoelectric effect of the piezoelectric element 42. A voltage is generated between the upper electrode 43 and the lower electrode 44 in each element 23. The voltage is output as an electric signal from the common interconnect terminals 29 and 32 and the signal interconnect terminals 31 and 33. Ultrasonic waves are thereby detected.

Transmission and reception of ultrasonic waves are repeated. As a result, linear scanning or sector scanning is realized. When scanning is completed, an image is formed based on digital signals of the output signals. The formed image is displayed on a screen of the display panel 15.

A laminated structure is established by the surface layer film 52 and the insulating film 24 in the ultrasonic device 17. The surface layer film 52 and the insulating film 24 form the vibrating film 41. The piezoelectric element 42 is formed on the vibrating film 41 for each opening 53. The vibrating film 41 and the piezoelectric element 42 form the element 23. Here, the conductor constituting the interconnect layer 27 is disposed under the insulating film 24. The conductor constituting the interconnect layer 27 extends in a layer different from the upper electrode 43 and the lower electrode 44 of the piezoelectric element 42. Accordingly, the conductor constituting the interconnect layer 27 can have a spread not interrupted by the upper electrode 43 and the lower electrode 44. The conductor constituting the interconnect layer 27 can function as a bus interconnect for the piezoelectric element 42. Interconnect resistance can be reduced.

The interconnect layer 27 has a width that is larger than the width Wc of the first interconnect 46, the second interconnect 47, and the third interconnect 48. The interconnect layer 27, which is a conductor, can thereby function as a bus interconnect, which is a common interconnect, with respect to the piezoelectric elements 42 belonging to the element array 22. Interconnect resistance can be reduced. The layout density of the piezoelectric elements 42, and the layout density of the elements 23 can be increased, compared with the case in which a bus interconnect, which is a common interconnect, is laid out between the piezoelectric elements 42 every segment 26, for example.

Here, the piezoelectric elements 42 are arranged at an equal pitch in the element array 22. In the element array 22, as described above, a drive voltage is applied to the piezoelectric elements 42 every segment 26 in sequence according to line scanning or sector scanning. The vibrating film 41 vibrates according to the supply of the drive voltage. Since the piezoelectric elements 42 are arranged at an equal pitch, contamination by unwanted noises in transmitting ultrasonic waves can be prevented.

(3) Ultrasonic Device According to Second Embodiment

Figure 6:
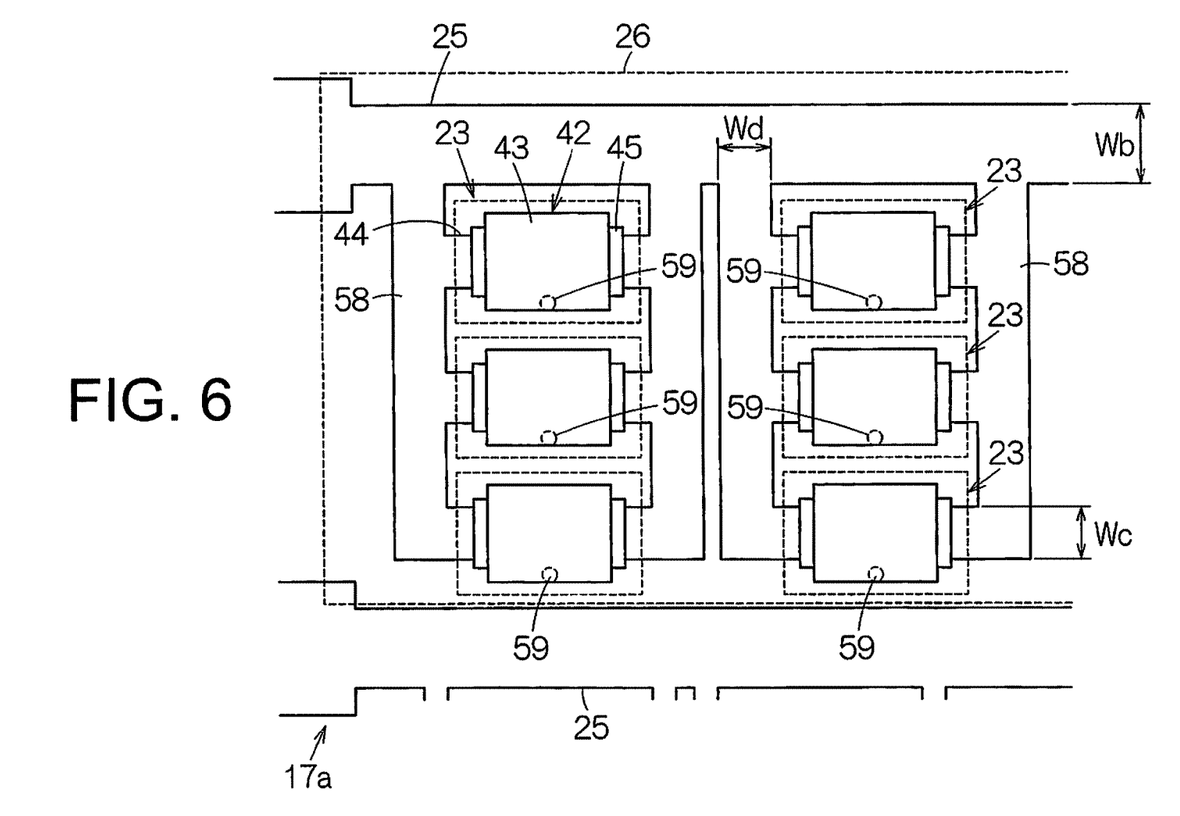
FIG. 6 is an enlarged partial plan view, corresponding to FIG. 4, of an ultrasonic device according to a second embodiment.

FIG. 6 shows an enlarged partial plan view of an ultrasonic device 17a according to a second embodiment. In the ultrasonic device 17a, an interconnect 58 is formed on a surface of the insulating film 24 in place of the first interconnect 46, the second interconnect 47, and the third interconnect 48. The interconnect 58 connects the lower electrodes 44 of the elements 23 in one row, in each segment 26, to the bus interconnect 25 electrically in parallel. In the interconnect 58, a width Wd of a portion to which elements 23 are commonly connected in parallel is larger than a width Wc of a portion that is continuous from each element 23. Note that Wc and Wd may be the same. Wc and Wd are smaller than a width Wb of the bus interconnect 25. A through conductor 59 is embedded in the insulating film 24 in each element 23. The through conductor 59, similarly to the through conductor 49, passes through the insulating film 24 from the surface of the insulating film 24 to the surface of the interconnect layer 27. The through conductor 59 connects the upper electrode 43 of each element 23 to the interconnect layer 27. The through conductor 59 may be continuous between the interconnect layer 27 and the upper electrode 43 of the element 23. The through conductor 59 can be formed by a conductive material similar to that of the upper electrode 43, for example. Accordingly, the piezoelectric films 45 in the same row are electrically connected in parallel between the bus interconnect 25 and the interconnect layer 27. The Other configurations are similar to those of the ultrasonic device 17 according to the first embodiment.

(4) Ultrasonic Device According to Third Embodiment

Figure 7:
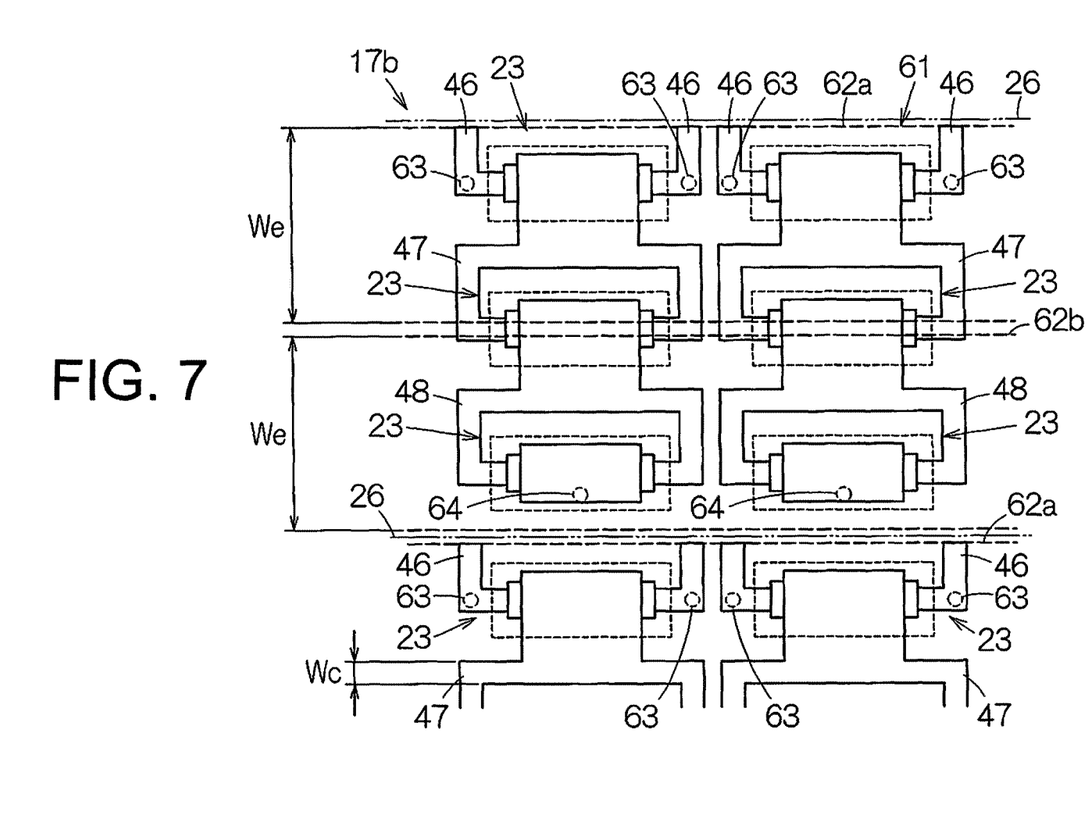
FIG. 7 is an enlarged partial plan view, corresponding to FIG. 4, of an ultrasonic device according to a third embodiment.

FIG. 7 shows an enlarged partial plan view of an ultrasonic device 17b according to a third embodiment. In the ultrasonic device 17b, an interconnect layer 61, which is a conductor, is used in place of the bus interconnect 25 on the insulating film 24. The interconnect layer 61, which is a conductor, is formed, under the insulating film 24, on the surface of the base 21. The conductor constituting the interconnect layer 61 includes a pair of conductive films 62a and 62b in each segment 26. The conductive films 62a and 62b extend in the column direction of the array. Here, two lines of the conductive films 62a and 62b are assigned for every three columns of elements 23. A conductive material such as copper may be used for the conductive films 62a and 62b. The bus interconnect on the surface of the insulating film 24 is thereby omitted. The Layout density of the element 23 can thereby be increased. Here, a width We of the conductive films 62 is larger than the width Wc of the first interconnect 46, the second interconnect 47, and the third interconnect 48.

A first through conductor 63 is embedded in the insulating film 24 for each element 23 in the first column. The first through conductor 63, similarly to the through conductor 49, passes through the insulating film 24 from the surface of the insulating film 24 to the surface of the interconnect layer 61. The first through conductor 63 connects the first interconnect 46 to one conductive film 62a. The first through conductor 63 may be continuous from the first interconnect 46 to the conductive film 62a. The first through conductor 63 can be formed by a conductive material similar to the material of the lower electrode 44, for example.

Similarly, a second through conductor 64 is embedded in the insulating film 24 for each element 23 in the third column. The second through conductor 64, similarly to the through conductor 49, passes through the insulating film 24 from the surface of the insulating film 24 to the surface of the interconnect layer 61. The second through conductor 64 connects the upper electrode 43 of the element 23 in the third column to the other conductive film 62b. The second through conductor 64 may be continuous from the upper electrode 43 of the element 23 in the third column to the conductive film 62b. The second through conductor 64 can be formed by a conductive material similar to the material of the upper electrode 43, for example. Accordingly, the piezoelectric films 45 in the same row are electrically connected in series from the conductive film 62a to the conductive film 62b. The other configurations are similar to those of the ultrasonic device 17 according to the first embodiment.

Figure 8:
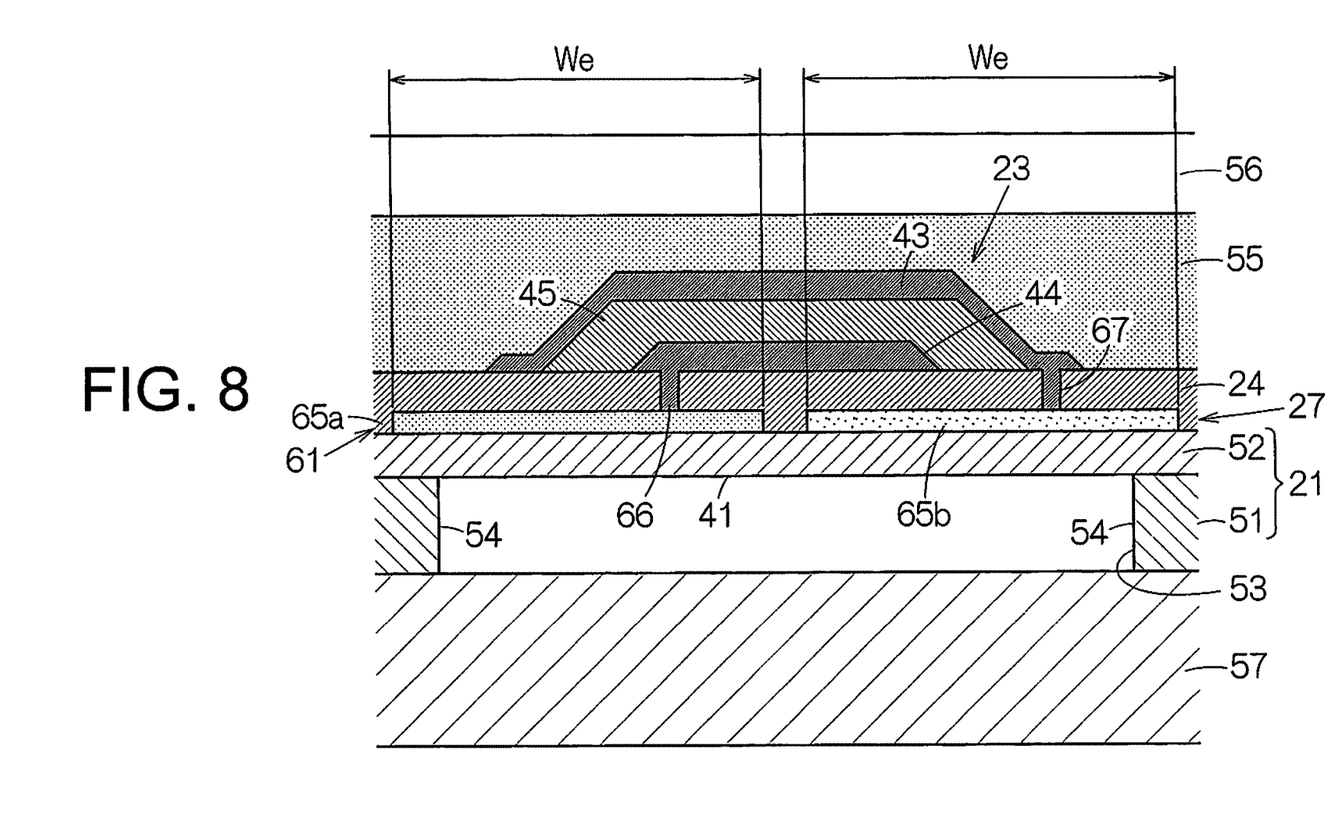
FIG. 8 is an enlarged cross-sectional view, corresponding to FIG. 5, of an ultrasonic device according to a modification of the third embodiment.

In addition, as shown in FIG. 8, conductive films 65a and 65b of the interconnect layer 61 may be assigned for each column of elements 23. Similarly to the above-described case, it is desirable that the width We of the conductive films 65a and 65b is larger than the width Wc of interconnects of the first interconnect 46 and the like. Here, a first through conductor 66 connects the lower electrode 44 of the element 23 to the conductive film 65a. The first through conductor 66 may be continuous from the lower electrode 44 to the conductive film 65a. A second through conductor 67 connects the upper electrode 43 to the conductive film 65b. The second through conductor 67 may be continuous from the upper electrode 43 to the conductive film 65b.

Note that although the present embodiment has been described in detail above, a person skilled in the art will appreciate that numerous modifications can be made without departing in substance from the novel matter and effects of the invention. Accordingly, all such modifications are within the scope of the invention. For example, terms that appear in the description or drawings at least once together with other broader or synonymous terms can be replaced by those other terms at any place within the description or drawings. Also, the configurations, operations and the like of the ultrasonic diagnostic apparatus 11, the apparatus terminal 12, and the element 23 are not limited to those described in the present embodiments, and various modifications can be made.

The entire disclosure of Japanese Patent Application No. 2013-203478, filed Sep. 30, 2013 is expressly incorporated by reference herein.

What is claimed is:

1. An ultrasonic device comprising:
  a base which defines a plurality of openings disposed in an array, and in which a base layer is formed and arranged respectively corresponding to each one of the openings;
  an interconnect layer which is a conductor, and is formed on the base layer in a thickness direction of the base;
  an insulating film that is formed on the interconnect layer in the thickness direction of the base, the insulating film and the base layer establishing a laminated structure to form a vibrating film, the insulating film and the base layer sandwiching the interconnect layer therebetween;
  a plurality of piezoelectric elements that are separated from the interconnect layer by the insulating film, the piezoelectric elements each including a first electrode and a second electrode that sandwich a piezoelectric film on the insulating film; and
  a through conductor that passes through the insulating film in the thickness direction of the base, and connects at least one of the first electrode and the second electrode to the conductor constituting the interconnect layer.

2. The ultrasonic device according to claim 1, wherein the conductor constituting the interconnect layer has a width that is larger than a width of an interconnect that connects the first electrode and the second electrode of two adjacent piezoelectric elements.

3. The ultrasonic device according to claim 1, wherein the interconnect layer is formed by an unpatterned film of a conductive material that is connected in common to all of the piezoelectric elements in the array.

4. The ultrasonic device according to claim 3, wherein all of the piezoelectric elements are arranged at an equal pitch in the array.

5. A probe comprising:
  the ultrasonic device according to claim 1, and
  a casing that supports the ultrasonic device.

6. An electronic device comprising:
  the ultrasonic device according to claim 1, and
  a processing apparatus that is connected to the ultrasonic device, and processes an output of the ultrasonic device.

7. An ultrasonic imaging apparatus comprising:
  the ultrasonic device according to claim 1, and
  a display apparatus that displays an image that is generated from an output of the ultrasonic device.

* * * * *